(12) United States Patent
Huang et al.

(10) Patent No.: US 8,709,071 B1
(45) Date of Patent: Apr. 29, 2014

(54) STENT WITH PREFERENTIAL COATING

(75) Inventors: Bin Huang, Pleasanton, CA (US); David C. Gale, San Jose, CA (US); Daniel A. Castro, Santa Clara, CA (US); Vincent J. Gueriguian, San Fancisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 372 days.

(21) Appl. No.: 11/864,472

(22) Filed: Sep. 28, 2007

(51) Int. Cl.
  *A61F 2/06* (2013.01)
(52) U.S. Cl.
  USPC ........ 623/1.42; 623/1.43; 623/1.44; 623/1.46
(58) Field of Classification Search
  USPC ........................................ 623/1.1–1.54, 1.42
  See application file for complete search history.

(56) References Cited

U.S. PATENT DOCUMENTS

| | | | |
|---|---|---|---|
| 5,605,696 A * | 2/1997 | Eury et al. | 424/423 |
| 6,242,041 B1 | 6/2001 | Katoot et al. | |
| 6,395,326 B1 | 5/2002 | Castro et al. | |
| 6,626,939 B1 | 9/2003 | Burnside et al. | |
| 2002/0051730 A1 | 5/2002 | Bodnar et al. | |
| 2003/0229393 A1 | 12/2003 | Kutryk et al. | |
| 2004/0071861 A1 | 4/2004 | Madrusov et al. | |
| 2004/0098090 A1 | 5/2004 | Williams et al. | |
| 2004/0098095 A1 * | 5/2004 | Burnside et al. | 623/1.13 |
| 2004/0249445 A1 * | 12/2004 | Rosenthal et al. | 623/1.15 |
| 2005/0004663 A1 * | 1/2005 | Llanos et al. | 623/1.46 |
| 2005/0019404 A1 * | 1/2005 | Sung et al. | 424/468 |
| 2005/0107870 A1 * | 5/2005 | Wang et al. | 623/1.44 |
| 2005/0124976 A1 * | 6/2005 | Devens et al. | 604/523 |
| 2005/0192662 A1 * | 9/2005 | Ward | 623/1.16 |
| 2006/0136048 A1 * | 6/2006 | Pacetti et al. | 623/1.42 |
| 2006/0149365 A1 | 7/2006 | Fifer et al. | |
| 2006/0155370 A1 | 7/2006 | Brister | |
| 2007/0003589 A1 | 1/2007 | Astafieva et al. | |
| 2007/0128723 A1 * | 6/2007 | Cottone et al. | 435/402 |
| 2009/0005860 A1 * | 1/2009 | Gale et al. | 623/1.44 |

FOREIGN PATENT DOCUMENTS

EP   0 970 711   1/2000

OTHER PUBLICATIONS

U.S. Appl. No. 11/128,099, filed May 11, 2005, Manicka et al.
U.S. Appl. No. 11/303,724, filed Dec. 16, 2005, Hossainy et al.
U.S. Appl. No. 11/820,344, filed Jun. 18, 2007, Fox et al.
U.S. Appl. No. 11/890,904, filed Aug. 7, 2007, Hossainy et al.
Anonymous, *Coating Techniques, Air Knife Coating*, http://www.ferron-magnetic.co.uk/coatings/airknife.htm, printed Jul. 1, 2003, 1 page.
Anonymous, *Coating Techniques, Gravure Coating*, http://www.ferron-magnetic.co.uk/coatings/gravure.htm, printed Jul. 1, 2003, 2 pages.
Anonymous, *Coating Techniques, Reverse Roll Coating*, http://www.ferron-magnetic.co.uk/coatings/revroll.htm, printed Jul. 1, 2003, 2 pages.
Anonymous, *Coating Techniques, Gap Coating (Knife Over Roll, etc.)*, http://www.ferron-magnetic.co.uk/cotings/knife.htm, printed Jul. 1, 2003, 1 page.

(Continued)

*Primary Examiner* — David Isabella
*Assistant Examiner* — Jacqueline Woznicki
(74) *Attorney, Agent, or Firm* — Squire Sanders (US) LLP

(57) ABSTRACT

This invention relates to stents, a type of implantable medical device, with an antiproliferative coating and a prohealing luminal coating and methods of fabricating stents with an antiproliferative coating and a prohealing luminal coating.

7 Claims, 7 Drawing Sheets

(56) References Cited

OTHER PUBLICATIONS

Anonymous, *Hepain-coated stents cut complications By 30%*, Clinica 732, pp. 17 (Nov. 18, 1996), http://www.dialogweb.com/cgi/document?req=1061847871753, printed Aug. 25, 2003, 2 pages.
Anonymous, *Rolling Therapeutic Agent Loading Device for Therapeutic Agent Delivery or Coated Stent* (Abstract 434009), Res. Disclos. pp. 974-975 (Jun. 2000).
Crowe et al., *Absorption and Intestinal Metabolism of SDZ-RAD and Rapamycin in Rats*, Drug Metabolism and Disposition, vol. 27, No. 5, pp. 627-632 (1999).
De Scheerder et al., *Biocompatibility of polymer-coated oversized metallic stents implanted in normal procine coronary arteries*, Atherosclerosis, vol. 114, pp. 105-114 (1995).
Dev et al., *Kinetics of Drug Delivery to the Arterial Wall Via Polyurthane-Coated Removable Nitinol Stent: Comparative Study of Two Drugs*, Catheterization and Cardiovascular Diagnosis, vol. 34, pp. 272-278 (1995).
Devanathan et al., *Polymeric Conformal Coatings for Implantable Electronic Devices*, IEEE Transactions on Biomedical Engineering, vol. BME-27, No. 11, pp. 671-675 (1980).
Dichek et al., *Seeding of Intravascular Stents with Genetically Engineered Endothelial Cells*, Circulation, vol. 80, No. 5, pp. 1347-1353 (Nov. 1989).
EFD, *780S Series Spray Valves VALVEMATE™ 7040 Controller Operating Manual*, 24 pages (2002).
Hahn et al., *Glow Discharge Polymers as Coatings for Implanted Devices*, John M. Dalton Research Center, University of Missouri-Columbia and the Graduate Center for Materials Research, pp. 109-113 (1981).
He et al., *Assessment of Tissue Blood Flow Following Small Artery Welding with an Intraluminal Dissolvable Stents*, Microsurgery, vol. 19, No. 3, pp. 148-152 (1999).
Helmus, *Overview of Biomedical Materials*, MRS Bulletin, pp. 33-38 (Sep. 1991).
Herdeg et al., *Antiproliferative Stent Coatings: Taxol and Related Compounds*, Semin, Intervent. Cardioil., vol. 3, pp. 197-199 (1998).
Kelley et al., *Totally Resorbable High-Strength Composite Material*, Advances in Miomedical Polymers, vol. 35, pp. 75-85 (1987).
Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).
Lambert et al., *Localized Arterial Wall Drug Delivery From a Polymer-Coated Removable Metallic Stent*, Circulation, vol. 90, No. 2, pp. 1003-1011 (Aug. 1994).
Lemos et al., *Coronary Restenosis After Sirolimus-Eluting Stent Implantation*, Circulation, vol. 108, No. 3, pp. 257-260 (Jul. 22, 2003).
Levy et al., *Strategies For Treating Arterial Restenosis Using Polymeric Controlled Release Implants*, Biotechnology and Bioactive Polymers, pp. 259-268 (1994).
Martin et al., *Enhancing the biological activity of immobilized osteopontin using a type-1 collagen affinity coating*, J. Biomed. Meter. Res. 70A, pp. 10-19 (2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Miyazawa et al., *Effects of Pemirolast and tranilast on Intimal Thickening After Arterial Injury in the Rat*, J. Cardiovasc. Pharmacol., vol. 30, No. 2, pp. 157-162 (1997).
Nichols et al., *Electrical Insulation of Implantable Devices by Composite Polymer Coatings*, ISA Transactions, vol. 26, No. 4, pp. 57-62 (1987).
Nordrehaug et al., *A Novel Biocompatible Coating Applied to Coronary Stents*, EPO Heart Journal 14, p. 321 (P1694), Abstr. Suppl. (1993).
Ohsawa et al., *Preventive Effects of an antiallergic Drug, Pemirolast Potassium, on Restenosis After Percutaneous Translumina Coronary Angioplasty*, American Heart Journal, vol. 136, No. 6, pp. 1081-1087 (Dec. 1998).
Peng et al., *Role of Polymers in improving the results of stenting in coronary arteries*, Biomaterial, vol. 17, pp. 685-694 (1996).
Prabhu, *Computational Modeling in Stent-based Drug Delivery*, Business Briefing: Medical Device Manufacturing & Technology, 4 pages (2004).
Saotome, et al., *Novel Enzymatically Degradable Polymers Comprising α-Amino Acid, 1,2-Ethanediol, and Adipic Acid*, Chemistry Letters, pp. 21-24, (1991).
Sono Tek Corporation, *AccuMist™ for Single Stent Coating Applications*, http://www.sono-tek.com/biomedical/accumist_stent.html, printed Aug. 2, 2005, 3 pages.
Sono Tek Corporation, *MediCoat™ DES 1000, Benchtop Stent Coating System*, http://www.sono-tek.com/biomedical/medicoat_standalone.html, printed Aug. 2, 2005, 4 pages.
Sono Tek Corporation, *MicroMist for Stent Coating*, http://www.sono-tek.com/biomedical/micromist_stent.html, printed Aug. 2, 2005, 3 pages.
Specially Coating Systems, *Parylene, a Biostable Coating for Medical Application*, 6 pages (no date).
Spagnuolo et al., *Gas1 as inued by VE-cadherin and vascular endothelial growth factor and inhibits endothelial cells apoptosis*, Blood vol. 103, No. 8, pp. 3005-3012 (2004).
Tsuji et al., *Biodegradable Polymeric Stents*, Current Interventional Cardiology Reports vol. 3, pp. 10-17 (2001).
Vapor Inc., *Vapore-Jet™ Capillary Pump—How it Works*, http://www.vapore.com/tech_howto.htm, printed Aug. 13, 2003, 2 pages.
Völkel et al., *Targeting of immunoliposomes to endothelial cells using a single-chain Fv Fragment directed against human endoglin (CD105)*, Biochemica et Biophysica Acta, vol. 1663, pp. 158-166 (Apr. 15, 2004).
von Recum et al., *Degradation of polydispersed poly(L-lactic acid) to modulate lactic release*, Biomaterials, vol. 16, pp. 441-445 (1995).
Wilensky et al., *Methods and Devices for Local Drug Delivery in Coronary and Peripheral Arteries*, Trends Cardiovasc. Med., vol. 3, No. 5, pp. 163-170 (1993).
World Precision Instruments, Inc., http://www.wpiinc.com/WPI_Web/Pumps/pneumatic_Fig.gif, printed Sep. 30, 2002, 1 page.
World Precision Instruments, Inc., *Nanoliter injector*, http://www.wpiinc.com/WPI_Web/Microinjection/Nanoliter_Injector.html, printed Jun. 10, 2005, 3 pages.
World Precision Instruments, Inc., *Nanoliter Injector*, http://www.wpi-europe.com/products/microinjection/nanoliter.htm printed Jun. 10, 2005, 2 pages.
World Precision Instruments, Inc., *Pneumatic PicoPumps*, http://www.wpieurope.com/products/microinjection/picopumps.htm, printed Jun. 10, 2005, 4 pages.
World Precision Instruments, Inc., *Pneumatic PicoPumps*, http://www.wpiinc.com/WPI_Web/Microinjection/Pneumatic_PicoPumps.html, printed Jun. 10, 2005, 4 pages.

\* cited by examiner

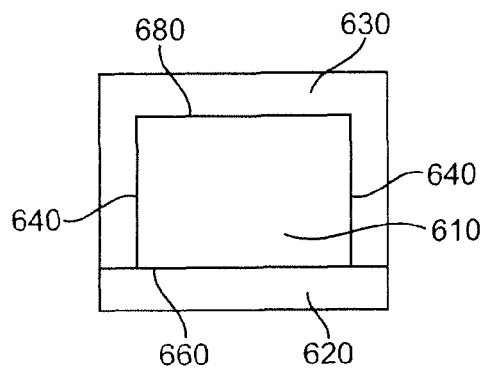
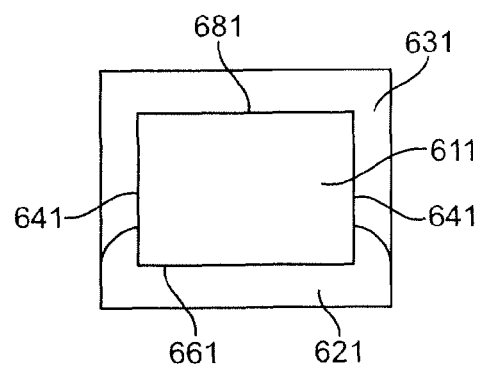
FIG. 6A
FIG. 6B
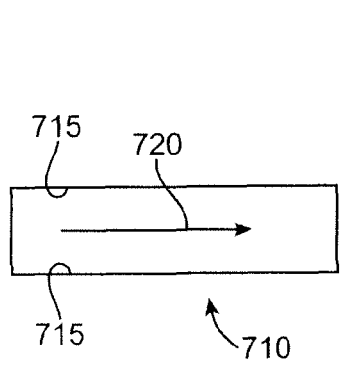
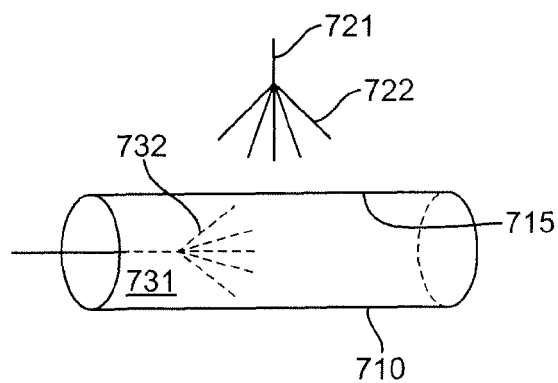
FIG. 7A
FIG. 7B

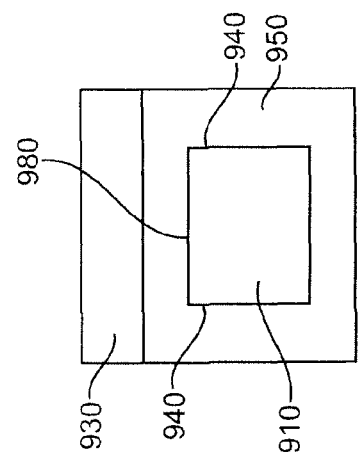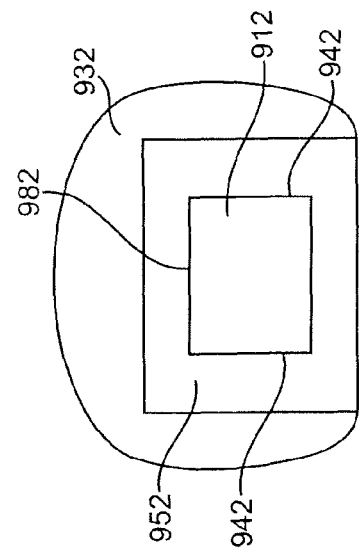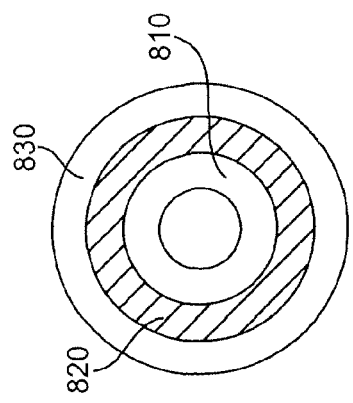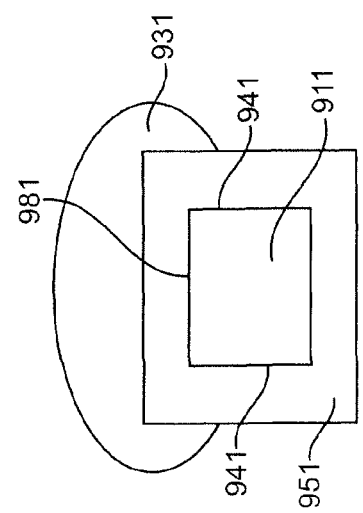

STENT WITH PREFERENTIAL COATING

BACKGROUND OF THE INVENTION

1. Field of the Invention

This invention relates to stents, a type of implantable medical device with a prohealing coating, and an antiproliferative coating selectively applied to the abluminal surface.

2. Background

This invention relates to stents, which, among other uses, are used in the treatment of artherosclerosis. Atherosclerosis is a progressive disease which results in build-up of materials such as fats, cholesterol, calcium and cellular debris, the build-up collectively referred to as plaques, within the walls of arteries. The build-up of plaque along the artery walls results in hardening and constriction of the artery. When an artery that provides blood to the heart is clogged, resulting in a loss of blood flow or a severe reduction in blood flow to the heart, a heart attack results. A clot in an artery leading to the brain, potentially resulting from dislodged arterial plaque, results in a stroke. Coronary artery disease, the hardening and narrowing of arteries to the heart often the resulting from artherosclerosis, is the leading cause of death in the United States for both men and women.

This invention relates, more generally, to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. The stent may be visualized during delivery and deployment using X-Ray fluoroscopy, if it contains radio-opaque materials.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated, and the catheter withdrawn. In the case of a self-expanding stent, the stent may be secured to the catheter via a constraining member, such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Once expanded, the stent must adequately maintain its size and shape throughout its service life despite the various forces that may come to bear on it, including the cyclic loading induced by the beating heart. In addition, the stent must possess sufficient flexibility to allow for crimping, expansion, and cyclic loading. Longitudinal flexibility is important to allow the stent to be maneuvered through a tortuous vascular path, and to enable it to conform to a deployment site that may not be linear, or may be subject to flexure. Finally, the stent should be biocompatible, so as not to trigger any adverse responses.

The structure of a stent is typically composed of scaffolding that includes a pattern, or network, of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier, or other carrier, that includes an active agent, bioactive agent, or drug. If the stent body includes a polymer, or the stent scaffolding is made from a polymer, the stent body may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

SUMMARY OF THE INVENTION

Various embodiments of the present invention include an implantable medical device including a stent body, a prohealing coating above a luminal surface of the stent body, the luminal coating of the stent body including a prohealing agent that promotes cell growth, and an antiproliferative coating above an abluminal surface, the antiproliferative coating of the stent body including an antiproliferative active agent.

Various embodiments of the present invention include an implantable medical device including a stent body, a prohealing coating above the surface of the stent body, the prohealing coating including a prohealing agent that promotes cell growth, and an antiproliferative coating above an abluminal surface of the stent body, the coating including an antiproliferative active agent.

Various embodiments of the present invention also include a method for coating a stent body, the method including crimping a stent body, forming a prohealing coating on a luminal surface of the stent body by applying a coating material including a prohealing agent that promotes cell growth on the luminal surface of the stent body, and forming an antiproliferative coating on an abluminal surface of the stent body by applying a coating material including an antiproliferative active agent on the abluminal surface of the stent body.

Various embodiments of the present invention also include a method for manufacturing a stent. The method includes forming a prohealing coating above an inner surface of a tube, the prohealing coating including a prohealing agent that promotes cell growth, forming a stent from the tube, and forming an antiproliferative coating above an abluminal surface of the stent, the antiproliferative coating of the stent including an antiproliferative active agent.

Some embodiments of the present invention include a method of manufacturing a stent from an extruded tube. The method includes forming a polymer tube including a middle layer, a prohealing layer, and an antiproliferative layer where the prohealing layer is on a luminal side of the middle layer, and the antiproliferative layer is on an abluminal side of the middle layer, and wherein the polymer tube is formed by co-extrusion of the layers. The stent is then formed from the tube.

Some embodiments of the present invention include a method for coating a stent body. The method includes forming a prohealing coating above all, or substantially all, of the surface of a stent body with a coating including a prohealing agent that promotes cell growth while the stent body is in an open configuration. Then an antiproliferative coating is selectively formed above an abluminal surface of the stent body, the antiproliferative coating including an antiproliferative active agent.

BRIEF DESCRIPTION OF THE DRAWINGS

FIGS. 6A-6B depict cross-sections of stent coatings according to some of the various embodiments of the present invention.
FIG. 7A depicts the flow of coating solution through a tube.
FIG. 7B depicts coating a tube.
FIG. 8 depicts the end view of a co-extruded tube.
FIGS. 9A-9C depict cross-sections of stent coatings according to some of the various embodiments of the present invention.

DETAILED DESCRIPTION OF THE INVENTION

Figure 1:
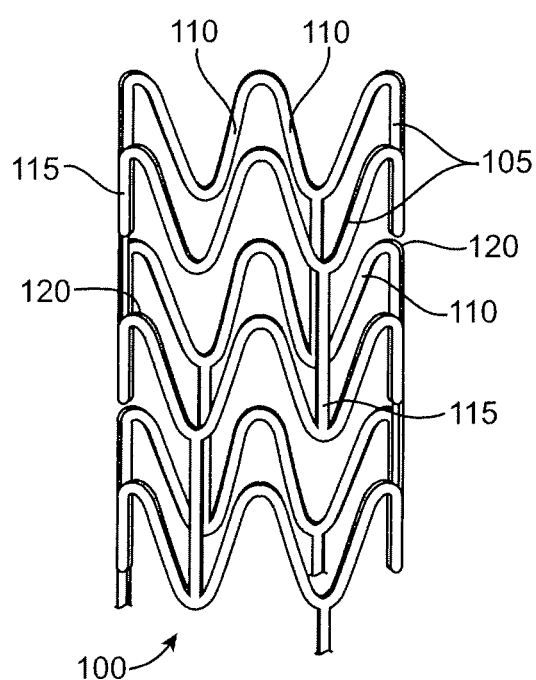
FIG. 1 depicts a view of a stent.

In the discussion that follows, to avoid the stilted language required to consistently indicate that the plural of various aspects of this invention is included with the singular and vice-versa, any reference to the singular implies the plural and visa-versa, unless expressly stated to be otherwise. For example, "a bioactive agent" or "the bioactive agent" will refer to a single bioactive agent or to a plurality of bioactive agents; "a polymer" or "the polymer" will refers to a single polymer or a plurality of polymers, etc.

Definitions

"Above" a surface or layer is defined as higher than or over a surface or layer measured along an axis normal to a surface, but not necessarily in contact with the surface or layer.

"Below" is defined as the opposite of "above."

"Cover" is defined as above and in contact with.

"Contiguous" is defined as being in actual contact or touching along a boundary or at a point.

"Prohealing agent" and "prohealing material" will be used interchangeably.

"Coating solution" will refer to a solution, or dispersion, of coating material in a solvent, or fluid, that may be sprayed or otherwise applied to a surface to create a film, or to otherwise deposit the coating material onto the surface. The solvent, or fluid, is removed, or substantially removed, during processing. Some residual solvent may be present in the coating material. In some cases, residual solvent may act as a plasticizer for the coating material. The term "coating solution" as used here will refer to true solutions as well as dispersions, including dispersions created with the aid of surfactants, or that require continuous mixing to prevent concentration gradients from forming in the container during the spray process. The "solvent" or carrier may be a liquid, gas or fluid.

"Conformal coating" will refer to a coating that is not selectively applied to an abluminal or luminal surface, but is applied to the entire surface of a medical device, even though there may be some portions of the surface without the conformal coating above the surface (in other words, the coating may not be above 100% of the surface).

As used herein, unless expressly stated otherwise, any words of approximation such as without limitation, "about," "essentially," "substantially" and the like mean that the element so modified need not be exactly what is described but can vary from the description by as much as ±15% without exceeding the scope of this invention.

Overview

Various embodiments of the present invention include a stent having a prohealing coating for promoting vascular healing on the luminal side, with an antiproliferative coating to reduce cell proliferation after deployment of the stent on the abluminal side. A body can include a plurality of structural elements including abluminal, luminal and sidewall surfaces. Various embodiments of the present invention include a stent having a prohealing coating covering all, substantially all (70%), or a significant fraction of the surface, and an antiproliferative coating to reduce cell proliferation after deployment of the stent on the abluminal side.

The various embodiments of the present invention are applicable to devices including, but not limited to, self-expandable stents, balloon-expandable stents, stent-grafts, and generally expandable tubular devices for various bodily lumen. In addition, various embodiments of the present invention include methods of manufacturing the stents, and applying coatings selectively to abluminal and luminal surfaces.

As outlined above, stents are used in the treatment of atherosclerotic stenosis in blood vessels. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

An example of a stent 100 is depicted in FIG. 1. The present invention is not limited to the stent pattern depicted in FIG. 1. In some embodiments, a stent may include a pattern or network of interconnecting structural elements or struts 105. Struts 105 of stent 100 include luminal faces or surfaces 110, abluminal faces or surfaces 115, and side-wall faces or surfaces 120. The pattern of structural elements 105 can take on a variety of patterns, and the structural pattern of the device can be of virtually any design. The embodiments disclosed herein are not limited to stents, or to the stent pattern, illustrated in FIG. 1. The embodiments are easily applicable to other patterns and other devices. The variations in the structure of patterns are virtually unlimited.

There are numerous methods of manufacturing stents. In some embodiments, a stent such as stent 100 may be fabricated from a tube by laser cutting, or chemical etching, a pattern of struts in the tube. In an exemplary embodiment, the tube can be cut with a laser, such as a femtosecond laser. The stent may also be formed by laser cutting or chemical etching of a polymeric sheet, rolling the pattern into the shape of the cylindrical stent, and providing a longitudinal weld to form the stent. Methods of forming a longitudinal weld are known in the art.

One difficulty presented by stenting is new intimal growth, neointima which is a new layer of endothelial cells that forms after stenting which resides between the internal elastic lamina and the vessel lumen. Another problem is inflammation of vascular tissue caused by the presence of the stent. Bioabsorbable polymeric stents, in particular, can trigger acute or chronic inflammatory responses due to the degradation of the stent. The vascular response to a fully bioabsorbable stent can be much different than that of a metal or polymer coated stent. Additionally, the re-endothelialization of the arterial lumen is critical for the healing response of the vessel. Without a healthy endothelium, the red blood cells will be prone to activation leading to thrombi.

Various embodiments of the present invention include a prohealing agent above the luminal surface, or above the surface, of the stent body. A prohealing material refers to a material that has the property that it promotes, or enhances, re-endothelialization of arterial lumen to promote healing of the vascular tissue. In addition, an antiproliferative agent can be included in a coating above the abluminal side of the stent to prevent, slow, or ameliorate, the proliferation of cells along the lumen wall. An antiproliferative agent is one that prevents, or inhibits, the proliferation of cells. Thus, the antiproliferative agent in the coating above the abluminal side of the stent body prevents excessive proliferation of cells, or hyperplasia, after stenting. The prohealing agent in the coating above the surface, or specifically above the luminal surface, ameliorates the impact of the antiproliferative on the re-endothelialization of the of the vascular tissue.

Preferentially Coated Stents and Methods for Preferential Coating

Various embodiments of the present invention include a stent including a stent body with a prohealing coating above a luminal surface of the stent body, where the prohealing coating includes a prohealing agent that promotes cell growth. These various embodiments also include an antiproliferative coating above an abluminal surface of the stent body where the antiproliferative coating includes an antiproliferative agent.

Some embodiments of the present invention include methods for selectively coating the luminal and abluminal surfaces of a stent. In the various embodiments to be described, "prohealing coating" will refer to a coating including a prohealing agent which is applied selectively above a luminal surface. In the various embodiments to be described, "antiproliferative coating" will refer to a coating including an antiproliferative agent which is applied selectively above an abluminal surface.

Figure 2A:
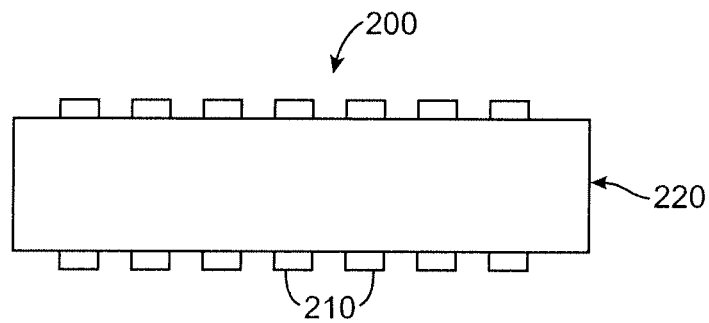
FIG. 2A depicts a stent crimped onto a mandrel.

In some embodiments, the stent is crimped down to a smaller diameter, such as the diameter that will be needed for delivery, for application of a coating. FIG. 2A illustrates a stent 200 which has been crimped down onto mandrel 220, where FIG. 2A represents a sectional view cut along the longitudinal centerline of mandrel 220. The struts 210 of the stent scaffolding are close together in the crimped state as compared to the open, or uncrimped state. A mandrel is a rod or bar, typically made of metal, around which a material may be shaped, or a spindle or axel used to support material for milling or machining. In this case, the mandrel would be cylindrically shaped object, used for crimping a stent, or alternatively, supporting a stent.

Figure 2B:
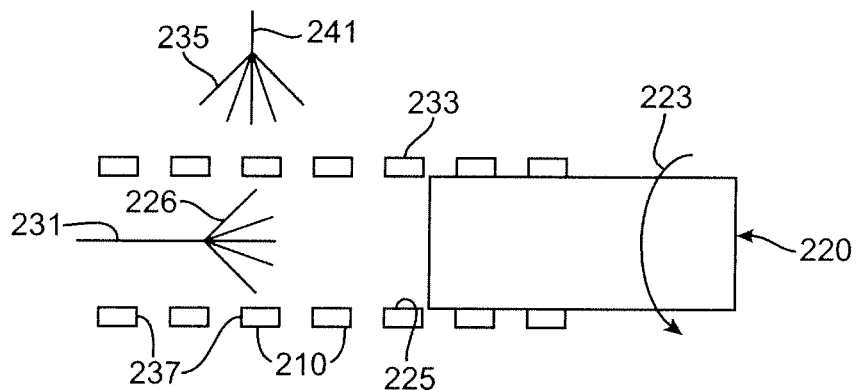
FIGS. 2B-2C illustrate methods of spraying a crimped stent.

The prohealing coating may be selectively applied to a luminal surface as illustrated in FIG. 2B, also a sectional view. After the stent has been crimped down as depicted in FIG. 2A, the mandrel 220 is partially removed as illustrated in FIG. 2B. The stent is supported on the end of mandrel 220. The luminal side 225, or inner side, of the crimped stent may be coated by inserting a sprayer nozzle 231 inside of stent 200 as illustrated in FIG. 2B. Nozzle 231 sprays a coating solution 226 over the luminal surface 225. The coating material remains on the luminal surface 225 after the solvent is removed, or substantially removed, forming a film or layer. Removal of the solvent may require air or gas flow, which may or may not be heated, over the surface after deposition on the surface, and/or during the coating operation. Some of the solvent is vaporized during the spraying process. The stent may be rotated in some manner, such as for example as shown by arrow 223, to ensure a uniform, or more or less uniform, coating.

As shown in FIG. 2B, since the struts 210 are close together, the sidewalls 237 and abluminal surface 233 of the struts are at least partially shielded from coating solution 226. The end of the stent supported by the mandrel could be sprayed in a similar manner by placing a second mandrel in the opposite side, removing mandrel 220 from the end, attaching the spray nozzle to another mandrel (not illustrated) and inserting the spray nozzle in the end from which mandrel 220 was just removed. The second mandrel, used to support the stent during coating, can be modestly smaller in diameter than mandrel 220 to prevent damage to the luminal coating.

As illustrated in FIG. 2B an antiproliferative coating layer may be formed by spraying the abluminal side 233 of the stent with a coating solution 235 from a spray nozzle 241. Again, in the crimped state, the struts 210 are close together, which reduces or prevents the exposure of the sidewalls 237 to the coating solution 235 from spray nozzle 241, and therefore, coating material is not deposited on the sidewalls 237. As with the prohealing coating, application of air or gas flow, optionally heated, is used to remove, or substantially remove, the solvent. In some embodiments, the antiproliferative layer may be applied to the abluminal surface at the same time as the prohealing layer is applied to the luminal surface. In other embodiments, the antiproliferative layer may be applied prior to the application of the prohealing layer. In still other embodiments, the antiproliferative layer may be applied after the prohealing layer has been applied.

Figure 2C:
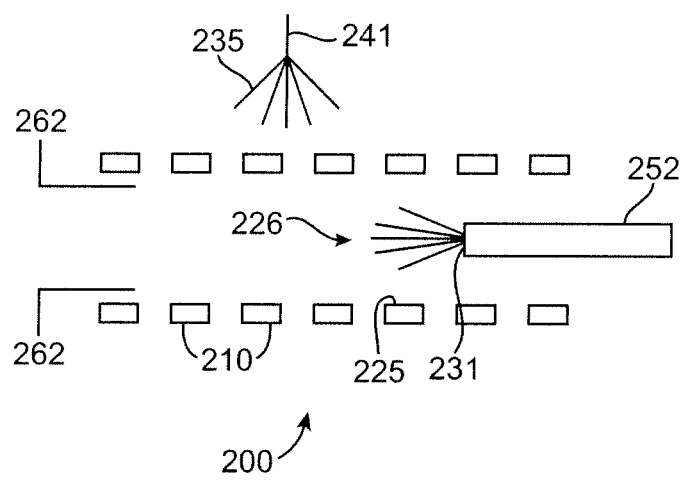

FIG. 2C illustrates an alternative manner of applying a coating selectively to a luminal surface. After crimping the stent onto mandrel 220 depicted in FIG. 2A, mandrel 220 is removed entirely. Stent 200 is placed on a support 262 that supports one end of stent 200. A mandrel 252 of smaller diameter than mandrel 220 of FIG. 2A, with the sprayer nozzle 231 attached to the end, may be used to spray coating solution 226 onto the luminal surface 225 of the stent. Similar to the alternative outlined above, the antiproliferative layer may then be coated onto the abluminal surface by spraying coating solution 235 onto the outside of the stent with sprayer nozzle 241 either before, after, or simultaneously with, the application of the prohealing coating to the luminal surface.

In FIG. 2C, mandrel 252 may be a smaller diameter than the mandrel used for crimping down the stent to allow for free translation of the mandrel 252 along the axis at the center of the interior of the stent. Free translation of mandrel 252 allows for a more even coating. Therefore, a mandrel of smaller diameter may leave room for the supply lines for compressed air, or other gas (for atomizing coating solution) and coating solution. In another embodiment, the mandrel may be tube shaped so that the compressed air (or other gas) and coating solution lines may be disposed within the center of the mandrel.

Figure 3:
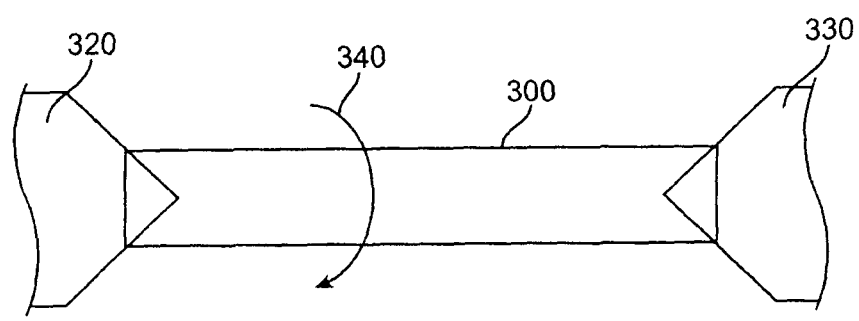
FIG. 3 depicts a stent on a support.

Instead of support 252 illustrated in FIG. 2C, the stent itself can be supported by a wire disposed along the axis of the stent or collets at the ends of the stent. FIG. 3 depicts stent 300 mounted between mandrel cones 320 and 330 to obtain 1:1 rotation between stent 300 and mandrel cones 320 and 330. Arrow 340 indicates the direction of rotation in one embodiment. The gap between the end rings of stent 300 and mandrel cones 320 and 330 can be adjusted to provide an optimal contact force to assure that mandrel cones 320 and 330, and stent 300, have the same, or substantially the same, axes of rotation. The contact force may be constrained such that it does not deform the stent.

Figure 4A:
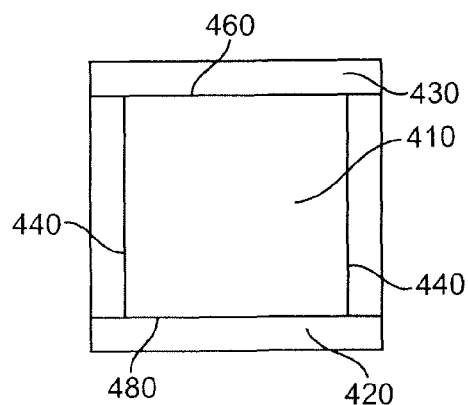
FIGS. 4A-4F depict cross-sections of stent coatings according to some of the various embodiments of the present invention.

FIG. 4A-4F are several depictions of cross-sections of a strut that may result from the application of the prohealing and antiproliferative coatings utilizing the methods outlined above. As depicted in FIG. 4A, an antiproliferative coating 430 above the abluminal surface 460 of strut 410 of the stent body, and a prohealing coating 420 above the luminal surface 480 of the strut. In this particular embodiment a mix of the antiproliferative and prohealing coatings is above the strut sidewalls 440. The stent body, including the strut 410, may be made of metal, polymer, or other materials, or any combination of the aforementioned materials.

Figure 4B:
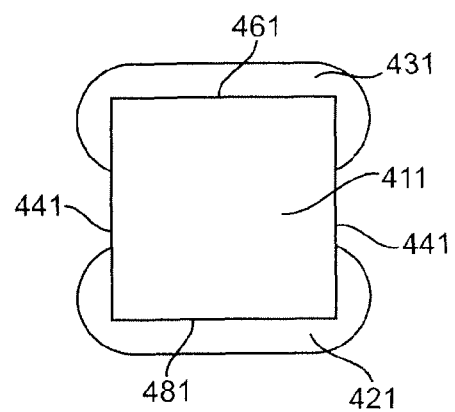

FIG. 4B depicts another embodiment in which the antiproliferative coating 431 is above the abluminal surface 461 of the strut 411 of the stent body, and a prohealing coating 421 above the luminal surface 481 of the strut. In this embodiment, the antiproliferative and prohealing coatings are above only part of the sidewalls 441, and do not contact each other.

Figure 4C:
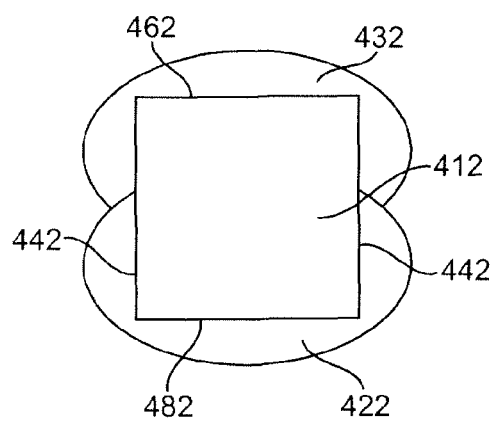

FIG. 4C depicts another embodiment in which the antiproliferative coating 432 is above the abluminal surface 462 and prohealing coating 422 above the luminal surface 482 of strut 412 of the stent body. Sidewalls 442 have the prohealing and antiproliferative coatings above the sidewall surface and the two coatings overlap, or partially overlap, each other. In some embodiments, the prohealing coating may be above the antiproliferative coating which is above the sidewall surface and in other embodiments it may be the opposite situation, that is the antiproliferative coating is above the prohealing coating which is above the sidewall surface.

Figure 4D:
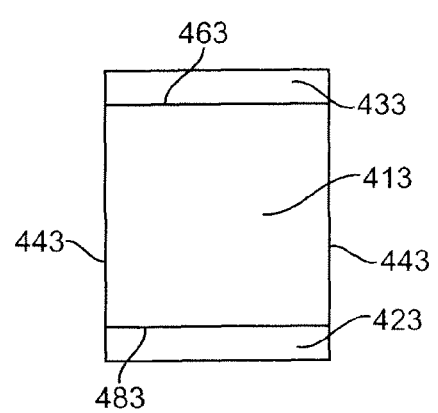

FIG. 4D depicts another embodiment in which the antiproliferative coating 433 and prohealing coating 423 are above the abluminal surface 463 and luminal surface 483, respectively, of strut 413 of the stent body, but the sidewalls 443 are free, or substantially free, of either the antiproliferative or prohealing coatings.

Figure 4E:
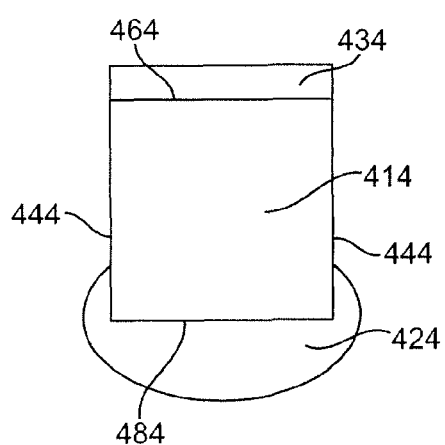
Figure 4F:
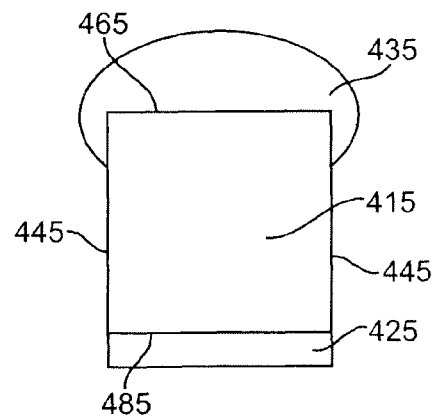

FIG. 4E depicts another embodiment in which the antiproliferative coating 434 and prohealing coating 424 are above the abluminal 464 and luminal surfaces 484, respectively, of strut 414 of the stent body, but the sidewalls 444 are free, or substantially free, of the antiproliferative coating, and part of prohealing coating is above a portion of sidewall 444 surface. The opposite situation is depicted in FIG. 4F in which the antiproliferative coating 435 and prohealing coating 425 are above the abluminal 465 and luminal 485 surfaces, respectively, of strut 415 of the stent body, but the sidewalls 445 are free, or substantially free, of the prohealing coating, and part of antiproliferative coating is above a portion of sidewall 445 surface. In the embodiments depicted in FIGS. 4E and 4F, the fraction of the sidewall surface with antiproliferative or prohealing coating above, respectively, may be about 10%, 15%, 20%, 30%, 40% or even 50%, or even about 60% or 70%.

The method of crimping the stent, followed by coating a luminal side, and then coating the abluminal side, as outlined above, can result in a structure such as that depicted in FIG. 4A, 4B, or 4C when crimping does not completely shield the sidewalls. The structures depicted in FIGS. 4D, 4E and 4F can result when crimping the stent completely shields the sidewalls from one or both coating solutions.

The structure depicted in FIG. 4C may result if both the sidewalls are coated with both the antiproliferative and prohealing coatings. The structure in FIG. 4C results if the prohealing coating is applied first, and allowed to dry. The prohealing coating may be partially above the antiproliferative coating above the sidewall surface, if the antiproliferative coating is applied first, and then allowed to dry. The opposite structure is possible if the prohealing coating is applied first.

The embodiments depicted in FIGS. 4D, 4B and 4C represent embodiments along a continuum where a substantial fraction, such as 80% to 90% or more, of the sidewall surface is free of, or substantially free of, both the antiproliferative and prohealing coatings, to an embodiment where the sidewall surface is completely coated.

In other embodiments, either of, or both, coatings may be above a substantial fraction, such as 50%, 60%, 70%, 80% or 90% of the sidewall surface, with the remaining fraction free of, or substantially free of, both coatings. In other embodiments, a substantial fraction of the sidewall surface such as 50%, 60%, 70%, 80% or 90% may be free of, or substantially free of, both coatings.

In some embodiments of the type depicted in FIG. 4C, there may be substantial overlap of the prohealing and antiproliferative coatings, such that all, or substantially all, of the antiproliferative coating above the sidewall surface has prohealing coating above it, or vice-versa. In other embodiments, some fraction, such as 70%, 50%, 30%, 20%, or 10% of the antiproliferative coating above the sidewall surface, has prohealing coating above, or vice-versa. In some embodiments, the antiproliferative and prohealing coatings may only contact each other at the center without overlap, or without substantial overlap, of the two coatings, or in other words, the two coatings or layers, may be contiguous.

On the other hand, if the coatings are applied simultaneously, or if the first coating is not completely dry prior to the application of the second coating, or if the solvent or fluid used to apply the second coating partially dissolves, wets, and/or is adsorbed and/or absorbed by the first coating, the structure of FIG. 4A may result. In FIG. 4A there is no clear overlap of the coatings above the sidewall surface of the strut. In some embodiments, the two coatings may be interdispersed. In some embodiments, there may be sections above the sidewall surface where the two coatings are mixed or interdispersed, other sections with the prohealing coating above an antiproliferative coating, and still other sections with the antiproliferative coating above the prohealing coating, or any combination of the aforementioned. Any of the aforementioned embodiments may also have some sections above the sidewall surface which are free of, or substantially free of, both the antiproliferative and prohealing coatings. In some embodiments, the mixing of the two coatings above the sidewall surface may be non-uniform.

In the various embodiments in which both the prohealing and antiproliferative coatings are above all, or some fraction of, the sidewall surface, the ratio of antiproliferative coating to prohealing coating above the sidewall surface may be 0.1:1, 1:1, 2:1, 3:1, 4:1, 5:1, 6:1, 8:1 or 10:1, or vice-versa.

Figure 5A:
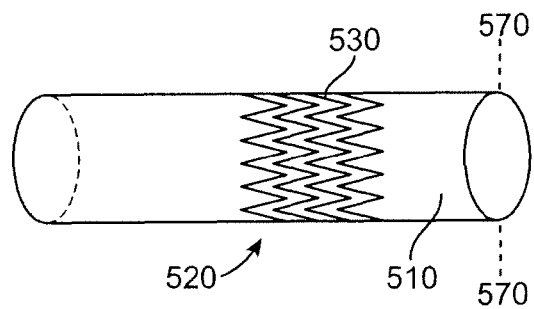
FIGS. 5A-5B depict a stent on a mandrel in the crimped, and uncrimped, configurations, respectively.

In another embodiment of the present invention, the exterior, or antiproliferative coating may be applied by masking the luminal, or interior, surface of the stent. Once the interior luminal surface has been coated, the stent may be placed on a mandrel, or other cylindrically shaped, or substantially cylindrically shaped, object, and then the abluminal surface sprayed with a coating solution. As depicted in FIG. 5A, the stent 520 is crimped down to a smaller diameter on mandrel 510. The struts 530 which make up the stent scaffolding are close together. Line 570-570 of FIG. 5A represents the plane corresponding to the longitudinal sectional view depicted in FIG. 5C which is analogous to FIG. 2A. Struts 530 of stent 520 are crimped close together onto mandrel 510 as shown in the sectional view depicted in FIG. 5C. After crimping, the stent may then be sprayed with a coating solution, or dipped in a coating solution. The mandrel shields the luminal surface so that the resulting structure may be that depicted in FIG. 4A, 4B, or 4C. In some embodiments, the structure may be that shown in FIG. 4F if the struts are sufficiently close together to shield the sidewalls from exposure to the antiproliferative coating, and the prohealing coating is applied to the luminal side in such a manner to shield the sidewalls from exposure to the prohealing coating. If the sidewalls are shielded from exposure to only the antiproliferative, but not the prohealing coating, the structure depicted in FIG. 4E may be possible. In other embodiments, the abluminal surface may be coated as above, and then the luminal surface may be coated.

Figure 5C:
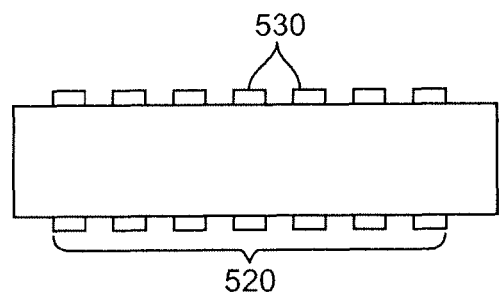
FIGS. 5C-5D depict the longitudinal cross-sectional view of a stent on a mandrel in the crimped, and uncrimped, configurations, respectively.
Figure 5B:
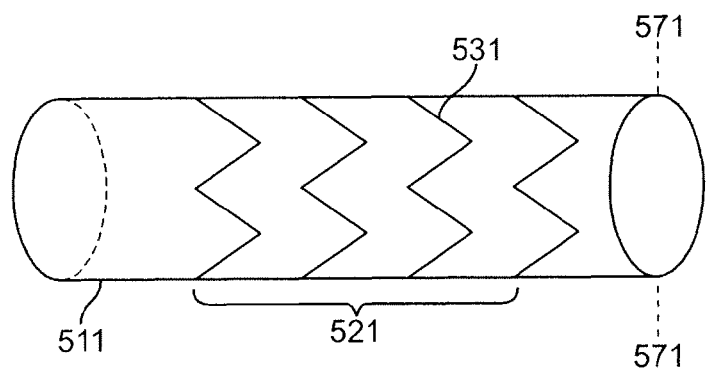
Figure 5D:
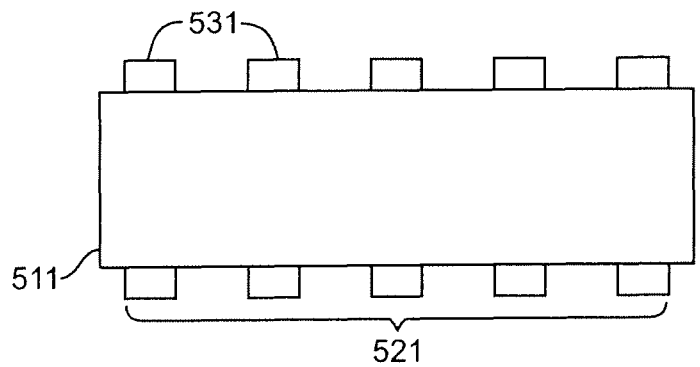

In further embodiments, as depicted in FIG. 5B, the stent 521 may be placed over a larger mandrel 511 in the uncrimped state, also referred to as the open configuration. Line 571-571 of FIG. 5B represents the plane corresponding to the longitudinal sectional view depicted in FIG. 5D. The struts 531 are wider apart in FIG. 5B as compared to FIG. 5A. Similarly, struts 531 of stent 521 are not crimped onto mandrel 511 as shown in the sectional view depicted in FIG. 5D, and are therefore wider apart than the struts 530 of FIG. 5C. The stent may then be coated by spraying the exterior of the stent, or dipping the stent into a coating solution. The resulting structure may be that depicted in FIG. 4A, or FIG. 4C. Due to the large spaces between the struts, as depicted in FIGS. 5B and 5D, the structures depicted in FIGS. 4B, 4D, 4E and 4F are unlikely to result.

FIG. 6A depicts another structural embodiment that may result from coating the stent in the open configuration. An antiproliferative coating 630 and prohealing coating 620 are above the respective abluminal 680 and luminal 660 surfaces of strut 610 of the stent body. In addition, the antiproliferative coating 630 is also above the sidewalls 640. FIGS. 4D, 4F and 6A represent a continuum of structures wherein the sidewall surface is free of, or substantially free of, the prohealing coating. Along this continuum, the sidewall surface may be free of, or substantially free of, the antiproliferative coating, as depicted in FIG. 4D, or the antiproliferative coating may be above all of, or substantially all of, the sidewall surface as depicted in FIG. 6A, or above only part of the sidewall surface as depicted in FIG. 4F. In some embodiments, the sidewalls 640, may be free of, or substantially free of, the prohealing coating.

In some embodiments, as depicted in FIG. 6B, the antiproliferative coating 631 is above the abluminal surface 681, and the prohealing coating 621 is above the luminal surface 661. There may be some prohealing coating 621 above the sidewalls 641, as well as the antiproliferative coating 631 above the sidewalls 641, as depicted in FIG. 6B. The antiproliferative and prohealing coatings may be partially interdispersed above the sidewall 641. In other embodiments, the antiproliferative coating may be above, or substantially above, the prohealing coating where both coatings are present. In some embodiments, the sidewalls 641 may have some sections that are free of, or substantially free of, both the antiproliferative coating and the prohealing coating. Some embodiments of the present invention include structures outlined in FIGS. 6A and 6B, but reversed with respect to the prohealing and antiproliferative coatings. These structures may be obtained by a number of methods such as masking the abluminal surface, and then coating the luminal surface.

As outlined above, in the various embodiments in which both the prohealing and antiproliferative coatings are above all, or some fraction of, the sidewall surface, the ratio of antiproliferative coating to prohealing coating above the sidewall surface may be 0.1:1, 0.5:1, 1:1, 2:1, 3:1, 4:1, 5:1, 6:1, 8:1 or 10:1, or vice-versa.

Masking of the luminal surface may be accomplished by numerous means. As illustrated in FIGS. 5A and 5B the masking can be accomplished by inserting a mandrel within the stent body. The mandrel outer diameter may be of a dimension such that the mandrel reduces, or prevents, the coating of, or substantially prevents the coating of, the luminal surface of the stent. This may be accomplished by using a mandrel that is a close fit to the inside diameter of the stent body, or an interference fit with the stent body.

Other manners of masking include the use of a hollow metal tube or other material with dimensions as outlined above. In some embodiments, the masking may be accomplished by the use of a tube which is made of a filter, or fiber, or other material that can adsorb and/or absorb overspray from the coating operation. In other embodiments, masking may be accomplished by use of a filter or other material disposed over, or stretched over, the exterior surface of a mandrel, rod, tube, or other stiff material. The rod, cylindrical, or tube-like object may be formed from a mesh, or screen, of metal, plastic or other material. Use of a mesh cylindrical object with a filter, cloth, or other material disposed over outer exterior surface may be particularly advantageous as it provides space for air flow through the center, thus improving the rate of solvent removal during the coating application process.

Various embodiments of the present invention include the fabrication of a stent from a tube. The prohealing coating on the interior, or luminal, surface can be applied by a number of methods, including flushing a coating solution through the tube, or otherwise providing for a flow of coating solution through the tube, such that the coating material deposits on the inside of the tube. FIG. 7A depicts a tube 710 through which the coating solution flows as shown by an arrow 720 to deposit coating solution on the inner surface 715 of the tube 710. The tube inside may be coated by alternatively flushing the tube with solution and then blowing air, or another gas, through to remove solvent, thus forming a coating, film, or layer, on the interior.

Alternatively, FIG. 7B depicts a spray nozzle 731 spraying coating solution 732 on the inner surface 715 of tube 710. A coating is formed on the inner surface when the solvent evaporates leaving a film of, or deposits of, coating material onto the tube's inner surface. An antiproliferative coating is formed on the exterior of the tube using a sprayer nozzle 721 such as that depicted in FIG. 7B that sprays coating solution 722.

In some embodiments, once the inner and outer diameter of the tube have been coated, the tube may be laser cut to form a stent pattern in the tube. The resulting structure of a strut may be that of FIG. 4D.

In alternative embodiments, the inside surface of the tube may be coated with a prohealing coating material, and a stent formed by laser cutting the tube. The exterior coating may be applied by masking the inner surface as described above, or use of other techniques known in the art. Thus, the method may produce embodiments depicted in FIG. 4B, or FIG. 4F. However, the most likely structures are those illustrated in FIG. 6A and FIG. 6B due to the exposure of the sidewall surfaces to the antiproliferative coating. Structures that are the reverse of FIGS. 6A and 6B may result if the exterior surface of a tube is coated first, and then the stent pattern cut into the tube, followed by prohealing coating using one of the methods outlined above, or another known in the art.

In still further embodiments, a tube may be formed by coextruding three layers. FIG. 8 is a depiction of a radial cross-section of a co-extruded tube with three layers, an inner or luminal layer 810, the body of the stent 820 which includes a polymer or other material that can be extruded, and the outer or abluminal layer 830. The stent may be formed by any number of methods including cutting a stent pattern into the tube with a laser, and then cutting the tube into smaller lengths, or alternatively, the tube may be cut into smaller lengths first, and then a stent pattern is cut into the tube sections. The structure resulting may be that illustrated in FIG. 4D. The structures in FIG. 4B, 4E, or 4F may result if one or both layers are distorted in the cutting process.

Further embodiments of the present invention include a stent having a prohealing coating covering all, substantially all, or a significant fraction of the surface ("conformal prohealing coating"), and an antiproliferative coating above the abluminal surface. In the embodiments to follow, the term "conformal prohealing coating" will refer to a coating including a prohealing agent that promotes cell growth. The conformal prohealing coating may be applied by standard methods known in the art.

Subsequent to the application of the conformal prohealing coating, the antiproliferative coating may be selectively applied to the abluminal surface by any one of a number of techniques. In one embodiment, the stent can be crimped as depicted in FIG. 5A and FIG. 5C, and the antiproliferative coating applied to the abluminal surface by standard spraying techniques. In other embodiments, the luminal side may be masked, and the coating applied to the exterior side by standard techniques, as outlined above. Masking may be done with the stent in the crimped configuration such as that depicted in FIGS. 5A and 5C, or the open configuration such as that depicted in FIGS. 5B and 5D. In other embodiments, the stent may be dipped into a coating solution.

Embodiments of the resulting structures of the aforementioned conformal prohealing coating and antiproliferative coating methods are illustrated in FIGS. 9A, 9B, and 9C. FIG. 9A depicts a strut 910 with a conformal prohealing coating 950 around strut 910 and an antiproliferative coating 930 above strut 910 abluminal surface 980. Sidewalls 940 are free of, or substantially free of, antiproliferative coating 930. The embodiment illustrated in FIG. 9A may result from coating the exterior of the stent in the crimped configuration with masking of the interior luminal surface.

Another structural embodiment that may result from exterior coating of the stent in the crimped configuration is depicted in FIG. 9B. Strut 911 has a conformal prohealing coating 951, and an antiproliferative coating 931 above the abluminal surface 981 of strut 911, and partially above the surface of sidewalls 941. FIG. 9B results when crimping allows exposure of the sidewalls to the coating solution.

Exterior coating of the stent with the stent in an open configuration may result in the structural embodiment illustrated in FIG. 9C. In FIG. 9C, strut 912 has a conformal prohealing coating 952 above the surfaces, and an antiproliferative coating 932 above the abluminal surface 982 of strut 912 as well as above all, or substantially all, or a significant fraction of, sidewalls 942.

The structures depicted in FIGS. 9A, 9B, and 9C represent a continuum of structures where the antiproliferative coating is above none, or substantially none, of the sidewall surface to a structure in which the antiproliferative coating is above all, or substantially all, of the sidewall surface. For some embodiments similar to that depicted in FIG. 9B, the antiproliferative coating may be above a fraction, such as, but not limited to, about 10%, 20%, 30%, 40%, 50%, 60%, 70%, or 80% of the sidewall surface, and also above the conformal prohealing coating to the extent that both coatings are present.

In still further embodiments of the present invention, the antiproliferative and/or prohealing coating may be applied utilizing a controlled deposition system ink-jet-type coating method that allows for the application of various substances only to certain targeted portions of a stent. A representative example of such a system, and a method of using the same, is described in U.S. Pat. No. 6,395,326 to Castro et al. A controlled deposition system can be capable of depositing a substance on stent body having a complex geometry, and otherwise apply the substance so that coating is limited to particular portions of the stent body, such as the abluminal surfaces of the struts of the stent body. The system can have a dispenser and a holder that supports the stent. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir, which holds a coating material or coating solution prior to delivery, and a nozzle having an orifice through which the coating material or coating solution is delivered. One exemplary type of dispenser assembly can be an assembly that includes an ink-jet-type printhead. Another exemplary type of a dispenser assembly can be a microinjector capable of injecting small volumes ranging from about 2 to about 70 nL, such as NANOLITER® 2000 available from World Precision Instruments, or PV830 PNUEMATIC PICOPUMPS® with Micropipette also available from World Precision Instruments. Such microinjection syringes may be employed in conjunction with a microscope of suitable design.

In some embodiments, the controlled deposition system may be used for applying both the prohealing and antiproliferative coatings, thus resulting in structures similar to the embodiments illustrated in FIG. 4D. If one of the antiproliferative or prohealing coatings is applied by the controlled deposition system, and the other is applied by a more conventional process, such as dipping or spraying, the structure in FIG. 4E, 4F, 6A or 6B may result. Similarly, in those embodiments utilizing the controlled deposition system for the application of an antiproliferative coating, the structure depicted in FIG. 9A may result, particularly if applied to the stent in the crimped state. If some of the antiproliferative or prohealing coating is applied above part of the sidewall surface, one of the other structures, such as 9B or 9C, may result.

Other methods may be used to selectively coat the luminal and abluminal surfaces of a stent. These include, but are not limited to, ink-jet-type coating, electrostatic coating, roll coating, thermal deposition with masking, plasma polymerization with masking, direct application of polymer/solvent solution by micro-syringe, direct polymer melt application, and spray coating with photomasking.

The various embodiments of the present invention also encompass variations in the thickness of the two coatings, the prohealing coating, and the antiproliferative coating. In some embodiments, the prohealing and the antiproliferative coating may be of the same, or substantially the same, thickness. In other embodiments, the antiproliferative coating may be thicker than the prohealing coating. In still other embodiments, the prohealing coating may be thicker than the antiproliferative coating.

The thickness of the coatings may range from about 0.1 to about 20 micrometers. More specifically, the thickness of the coatings may range from about 0.1 to about 1 micrometers, from about 1 to about 3 micrometers, from about 1 to about 5 micrometers, from about 2 micrometers to about 10 micrometers, from about 10 micrometers to about 20 micrometers, from about 5 micrometers to about 15 micrometers, or from about 5 micrometers to about 20 micrometers. An especially suitable range may be from 0.1 micrometers to 8 micrometers.

Additional Coatings

Various embodiments of the present invention including a prohealing coating, and an antiproliferative coating, may include additional coating layers. In some embodiments, the stent further includes an additional coating above both the antiproliferative and prohealing coating, or below both the antiproliferative and prohealing coatings. The latter will also be referred to as a "base coating." The base coating may include a polymer and/or one or more active agents. The base coating may provide any one of a number of functions such as, but not limited to, providing a surface for further coating, serving as a diffusion barrier or release controlling layer for active agent incorporated in the body of the stent, serving as a primer, or for aesthetic reasons.

In some embodiments, the base coating may be above all, or above substantially all, of the surface of the stent, or the base coating may be above only part of the surface of the stent. In other embodiments the base coating may be selectively applied such that it is above an abluminal surface of the stent, or in the alternative, above a luminal surface of the stent.

Various embodiments of the present invention may also include an additional top coating. The top coating is defined as a coating above the stent surface, and also above both of the prohealing and the antiproliferative coating. In some embodiments of the present invention, the stent further includes at least one top coating. The top coating may include a polymer and/or one or more active agents.

In some embodiments, the top coating may be above all, or above substantially all, of the surface of the stent, or the top coating may be above only part of the surface of the stent. In other embodiments the top coating may be selectively applied such that it is above an abluminal surface of the stent, or in the alternative, above a luminal surface of the stent.

The top coating may serve any one of a number of functions such as providing a protective layer, or allowing for easier insertion or handling, or acting as a carrier or matrix for one or more active agents. The top coat may be applied for aesthetic reasons, such as, but not limited to, to provide a uniform appearance if the antiproliferative and prohealing coatings, are significantly different in appearance. The top coating may also act as rate controlling layer for active agent incorporated in the coatings below the top coating and/or active agent incorporated within the body of the stent.

In some other embodiments, the additional coating layer will be above the surface of the stent body, but below either the antiproliferative coating or the prohealing coating and above the other of the antiproliferative coating or the prohealing coating. For example, one embodiment includes an additional coating layer that is above the antiproliferative coating above an abluminal surface, and below the prohealing coating which is above the luminal surface. The coating above one of the antiproliferative coatings or the prohealing coating, and below the other of the aforementioned coatings, will be referred to as an "interspersed coating." A coating may be above a conformal prohealing coating, but below an antiproliferative coating which is above the abluminal surface which will be referred to as a "middle coating." Various embodiments of the current invention include at least one middle and/or interdispersed coating. The middle or interdispersed coating may serve as a means to separate the prohealing agent and the antiproliferative agent.

Prohealing Coating and the Antiproliferative Coating

The prohealing coating, and the antiproliferative coating of the various embodiments will have a sufficient weight percent of the prohealing material, or agent, or antiproliferative agent, respectively, to provide a desired dose of the agent.

In some embodiments, the prohealing material may be between 10% and 80%; 20% and 70%; 30% and 60%; or 40% and 50% by weight of the coating, or in some other embodiments, not more than 10% or not less than 80% by weight of the coating. In still other embodiments, the prohealing material may be between 5% and 35%, 10% and 25%, 35% and 60%, or between 60% and 85%, by weight, of the coating.

Similarly, the antiproliferative agent may be between 10% and 80%; 20% and 70%; 30% and 60%; or 40% and 50% by weight of the coating, or in some other embodiments, not more than 10% or not less than 80% by weight of the coating. In still other embodiments, the antiproliferative material may be between 5% and 35%, 10% and 25%, 35% and 60%, or between 60% and 85%, by weight, of the coating.

The total drug dose in the coating for the prohealing material, or the antiproliferative agent will depend upon the specific agent used, the total dose to be administered and the duration of treatment. For the antiproliferative, the total drug in the layer may be between about 5 to about 15 ug/cm$^2$, 15 to about 25 ug/cm$^2$, 25 to about 50 ug/cm$^2$, about 50 ug/cm$^2$ to about 125 ug/cm$^2$, about 125 ug/cm$^2$ to about 300 ug/cm$^2$, about 300 ug/cm$^2$ to about 500 ug/cm$^2$, or higher.

The prohealing coating and the antiproliferative coating of the various embodiments of the present invention each include at least one prohealing material or antiproliferative agent, respectively. In some embodiments, the prohealing layer and/or the antiproliferative layer may include more than one prohealing material or antiproliferative agent, respectively. In addition, in some embodiments the prohealing layer may include an additional active agent. Similarly, in some embodiments the antiproliferative layer may include an additional active agent.

The prohealing coating and the antiproliferative coating of the various embodiments of the present invention may further include other materials, and in particular these coatings may include a polymer. Therefore, prohealing agents or antiproliferative agents can be mixed or dispersed within a biostable polymer, or a bioabsorbable polymer, or combinations thereof. The polymer may be cross-linked, either before, concurrently, or subsequent to the application to the stent body.

The composition of the prohealing coating, whether above a luminal surface of the stent body or a coating above the surface of the stent body, and the antiproliferative coating of the various embodiments, will also depend upon the desired release rate of the active agent(s). Thus, it may be desirable to release the antiproliferative agent over a period of a day, several days, a week, ten days, two weeks, a month, six weeks, or over a couple of months or three to four months. The duration of drug release may be as along as six months to a year.

The duration of the release of the antiproliferative agent or prohealing agent may, or may not, coincide with the duration of treatment with the stent. In those embodiments in which the stent body is bioabsorbable, the duration of the release of the antiproliferative agent or prohealing agent may be less than, or the same as, the time for degradation, or for substantial degradation, of the stent body. Degradation time refers to the time for the stent, or the bioabsorbable portion of the stent, to substantially, or completely, erode away from an implant site. At the time of complete degradation either no portion of the bioabsorbable stent, or no part of the bioabsorbable portion of the stent, remains, or very negligible traces or residue of the stent, remains.

The release profile of the antiproliferative agent and the prohealing agent can be of any number of profiles, such as but not limited to, zero-order release, exponential decay, step-function release or other release profiles that carry over a period of time. The terms "zero-order release", "exponential decay" and "step-function release" as well as other sustained release profiles are well known in the art (see, for example, Encyclopedia of Controlled Drug Delivery, Edith Mathiowitz, Ed., Culinary and Hospitality Industry Publications Services).

Prohealing Materials

A prohealing material refers to a material that has the property that it promotes or enhances re-endothelialization of arterial lumen to promote healing of the vascular tissue. The prohealing-containing coatings of the stent can attract, bind and eventually become encapsulated by endothelial cells. In certain embodiments, the prohealing agent in the prohealing coating of the stent attracts, binds, and becomes encapsulated by endothelial progenitor cells. The attraction, binding, and encapsulation of the cells will reduce or prevent the formation of emboli or thrombi due to the loss of the mechanical properties that could occur if the stent were made with a polymer, and if the stent were insufficiently encapsulated. In some embodiments, the enhanced re-endothelialization promotes the endothelialization at a rate faster than the loss of mechanical properties of the stent.

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing material can be an endothelial cell (EDC) binding agent. In some embodiments, the EDC binding agent can be protein, peptide and antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways (see, e.g., Martin, S. M., et al., J. Biomed. Mater. Res. 70A:10-19 (2004)). Endothelial cells can be selectively targeted (for the targeted delivery of immunoliposomes) using scFv A5 (Volkel, T., et al., Biochimica et Biophysica Acta 1663:158-166 (2004)). Junction membrane protein vascular endothelial (VE)-cadherin has been shown to bind to endothelial cells and down regulate apoptosis of the endothelial cells (Spagnuolo, R., et al., Blood 103:3005-3012 (2004)).

In some embodiments, the EDC binding agent can be the active fragment of osteopontin, (Asp-Val-Asp-Val-Pro-Asp-Gly-Asp-Ser-Leu-Ala-Try-Gly). Other useful EDC binding agents include EPC (epithelial cell) antibodies, RGD peptide sequences, RGD mimetics, and combinations thereof.

The EDC binding protein and peptide can be prepared according to the established methods, e.g., isolation and purification from natural sources, recombinant techniques, or combinatorial chemistry for the synthesis of peptides. For example, the active fragment of osteopontin can be readily prepared by combinatorial synthesis using, e.g., solid-phase peptide sequencing (e.g., a Merrifield synthesis). The scFv A5 protein can be synthesized by gene expression as described in the literature from the HisCysForNot(5'-TAG TGC GGC CGC TTA GCA TGC TCC GCC ATG GTG ATG GTG ATG ATG CGC ACG TTT GAT TTC CAG TTT GGT-3') (Volkel, T., et al., Biochimica et Biophysica Acta 1663: 158-166 (2004)).

In further embodiments, the prohealing material may a substance or agent that attracts and binds endothelial progenitor cells. Representative substances or agents that attract and bind endothelial progenitor cells include antibodies such as CD-34, CD-133, and vegf type 2 receptor. An agent that attracts and binds endothelial progenitor cells can include a polymer having nitric oxide donor groups.

In other embodiments, the EDC binding agent can be chemically linked to a polymer (e.g., via a linkage). The polymer can be the polymer of the coating or a polymer from which the device is made. For example, the active fragment of osteopontin can be attached to the acid terminal poly(lactic acid) via a PEG linkage.

The foregoing substances can also be used in the form of prodrugs or co-drugs thereof. The foregoing substances also include metabolites thereof, and/or prodrugs of the metabolites. The foregoing substances are listed by way of example and are not meant to be limiting. Other active agents which are currently available or that may be developed in the future are equally applicable.

Antiproliferative Agents

Antiproliferative agents are included to prevent excessive buildup of cells at the vessel wall, or hyperplasia, that may result from stenting. Examples of antiproliferative agents include, but are not limited to, pharmaceutical agents from the rapamycin analogs or paclitaxol. The drug acts on several cellular pathways including the FKBP/mTorr mediated signaling for a proliferative response. The control of the proliferative response of the smooth muscle cells, which results in the hyperplasia response to the stenting injury, is at the expense of a slow re-endothelialization of the lumen. There are numerous antiproliferative agents that are encompassed in the present invention.

An antiproliferative agent can be a natural proteineous agent such as a cytotoxin or a synthetic molecule. The active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof. In some embodiments, the anti-proliferative agent may be everolimus.

The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

Implantable Medical Device Body

The various embodiments of the present invention, may include a stent body which provides all, or substantially all, of the of the support for the bodily lumen. In other words, prior to any coating of the stent body, the stent body could be used to support a bodily lumen.

In some embodiments of the present invention, the stent body includes a metal or metallic alloy. The metal or metallic alloy may be biostable, or bioerodable. Biostable metals have negligible erosion or corrosion rates when exposed to bodily fluids. An erodable metal is one that has the propensity for self-dissolution in an in vivo environment, and a metal that undergoes self-dissolution in an in vivo environment corrodes when subjected to bodily fluids and breaks down.

The stent body can also include a biostable or biosorbable polymer, or combinations thereof. In general, polymers can be biostable, bioabsorbable, biodegradable, bioerodable, dissolvable, or water soluble. Biostable refers to polymers that are not bioabsorbable. The terms biodegradable, bioabsorbable, bioerodable, and biosoluble, as well as degraded, eroded, absorbed, and dissolved refer to polymers that are capable of being completely eroded or absorbed when exposed to bodily fluids such as blood and can be gradually resorbed, absorbed and/or eliminated by the body, and as used herein, the terms will be used interchangeably. The processes of breaking down and absorption of the polymer can be caused by, for example, hydrolysis and metabolic processes. In some embodiments utilizing a bioabsorbable polymer, very negligible traces or residue may be left behind.

As a bioabsorbable stent degrades, its mechanical properties degrade. A bioabsorbable stent may be configured to disintegrate and disappear from the region of implantation once treatment is completed. The duration of a treatment period depends on the bodily disorder that is being treated. For illustrative purposes only, in treatment of coronary heart disease involving use of stents in diseased vessels, the duration can be in a range from about a month to a few years. However, the duration is typically in a range from about six to twelve months, but in some case the duration may be only a month, two months, or three months. Thus, it is desirable for polymer-based coatings and substrates of a stent to have a degradation time at, or near, the duration of treatment with the stent. Degradation time refers to the time for stent to substantially, or completely, erode away from an implant site.

Materials for the Stent Body and/or Coatings

As outlined above, the various embodiments of the present invention include a stent body manufactured of a metal and/or polymer. In addition, the various coatings may include a polymer and/or other materials.

In general, representative examples of polymers that may be used in embodiments as of the present invention either part of the stent body, or as a coating above a surface of the stent body, include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoesters, polyanhydrides, poly(glycolic acid), poly(glycolide), poly(L-lactic acid), poly(L-lactide), poly(D,L-lactic acid), poly(L-lactide-co-glycolide), poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose, and/or combinations thereof.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. Other especially well-suited polymers for use as part of the stent body are poly(L-lactic acid), poly(L-lactide) ("PLLA"), poly(D,L-lactic acid), poly(L-lactide-co-glycolide) and poly(D,L-lactide) ("D,P-PLA").

In particular embodiments of the present invention, for utilization as the polymer for the stent body, the PLLA may have a weight average molecular weight from about 65,000 to about 100,000, about 100,000 to about 200,000, or about 175,000 to 250,000, or in some embodiments, even higher. In some embodiments, such PLLA polymers may have a crystallinity of about 10 to about 30%, about 30% to about 55%, about 55% to about 60%, or higher. For utilization as a component in a coating, the D,L-PLA polymer weight average molecular weight may be significantly lower, in the range of about 5,000 to about 80,000.

Any of the polymers may be cross-linked prior to use as part of a stent body, concurrent with the manufacture or after the manufacture. Similarly, any polymers used for a coating may be cross-linked before, concurrent with, or after coating application.

Any copolymer (two or more types of monomers), whether random, graft, or block copolymers, which includes any one or more of the polymers in the above list (and/or constituent monomers of the polymers in the above list), regardless of which other polymer, polymers, or monomers are included in the copolymer, and without regard for whether or not the other polymer, polymers, or monomers are specifically listed herein, is also encompassed in the current invention. Various embodiments of the current invention encompass both uncross-linked and cross-linked polymers.

The stent body may be fabricated from a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In some embodiments, the stent body may be manufactured from a combination of metals or metallic alloys, a combination of polymers, or a combination of one or more metals or metallic alloys and one or more polymers, with or without additional materials. In any of the aforementioned combinations of polymers, the combinations of polymers can include biodegradable polymers, bisostable polymers, and/or both.

Other Active Agents

Drugs, or therapeutic active agents not specifically classified as either antiproliferative agents or prohealing agents can also be included in the various embodiments of the present invention. The drugs or therapeutic active agent(s) can include anti-inflammatories, and other bioactive agents.

An anti-inflammatory drug can be a steroidal anti-inflammatory agent, a nonsteroidal anti-inflammatory agent, or a combination thereof. In one embodiment, the anti-inflammatory agent is clobetasol. Alternatively, the anti-inflammatory may be a biological inhibitor of proinflammatory signaling molecules. Anti-inflammatory biological agents include antibodies to such biological inflammatory signaling molecules.

These active agents can be any agent which is a therapeutic, prophylactic, or a diagnostic agent, or any agent which is used to treat a disease or condition. In some embodiments, such agents may be used in combination with antiproliferative or anti-inflammatory agents. These agents can also have antiproliferative and/or anti-inflammatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples also include antineoplastics and/or antimitotics, anticancer agents, dietary supplements such as various vitamins, cytostatic substances, antiallergic agents, and other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable. Embodiments of the present invention also include various combinations of the aforementioned active agents.

Dosage of Active Agents

The dosage or concentration of the active agent required to produce a favorable therapeutic effect should be less than the level at which the bioactive agent produces toxic effects and greater than the level at which non-therapeutic results are obtained. This applies to an antiproliferative agent, a prohealing agent, or any other active agent included in any of the various embodiments of the invention. Therapeutically effective dosages can also be determined from an appropriate clinical study, such as but not limited to, a Phase II or Phase III study. Effective dosages can also be determined by the application of an appropriate pharmacokinetic-pharmacodynamic model in human, or other animals. Standard pharmacological test procedures to determine dosages are understood by one of ordinary skill in the art.

Other Materials

All embodiments may also include additional components such as, but not limited to, lubricating agents, fillers, plasticizing agents, surfactants, diluents, mold release agents, agents which act as active agent carriers or binders, anti-tack agents, anti-foaming agents, viscosity modifiers, potentially residual levels of solvents, and potentially any other agent which aids in, or is desirable in, the processing of the material, and/or is useful, or desirable, as a component of the final product, or if included in the final product.

Terms such a "element", "member", "device", "section", "portion", "step", "means" and words of similar import when used herein shall not be construed as invoking the provisions of 35 U.S.C. §112(6) unless the following claims expressly use the term "means" followed by a particular function without specific structure or the term "step" followed by a particular function without specific action.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising:
    a stent body comprising a plurality of structural elements, each structural element comprising a luminal surface, an abluminal surface and a sidewall surface connecting the luminal surface to the abluminal surface, wherein the stent body is made of a bioabsorbable material which allows the stent body upon implantation to disintegrate, absorb and disappear from a region of implantation;
    a prohealing coating above and in contact with the luminal surface and the abluminal surface of the stent body, the prohealing coating comprising a prohealing agent that promotes cell growth; and
    an antiproliferative coating above and in contact with the prohealing coating that is above the abluminal surface of the stent body, the antiproliferative coating comprising an antiproliferative active agent,
    wherein the luminal surface of the stent body is free or substantially free of antiproliferative coating.

2. The stent of claim 1, wherein the prohealing coating is above all or substantially all of an entire surface of the stent body.

3. The stent of claim 1, wherein the stent body provides all or substantially all of the support for the bodily lumen.

4. The stent of claim 1, wherein the bioabsorbable material is a bioabsorbable polymer.

5. The stent of claim 1, wherein the prohealing coating comprises a substance selected from the group consisting of a protein, a peptide, an antibody that attracts and binds endothelial cells, a substance that attracts and binds endothelial progenitor cells, the antibody CD-34, the antibody CD-133, VEGF type 2 receptor, and any combinations thereof.

6. The stent of claim 1, wherein the antiproliferative coating comprises everolimus and the stent body comprises PLLA.

7. A stent comprising:
    a stent body comprising a plurality of structural elements, each structural element comprising a luminal surface, an abluminal surface and a sidewall surface connecting the luminal surface to the abluminal surface, wherein the stent body is made of a bioabsorbable material which allows the stent body upon implantation to disintegrate, absorb and disappear from a region of implantation;
    a prohealing coating above and in contact with the luminal surface and the abluminal surface of the stent body, the prohealing coating comprising a prohealing agent that promotes cell growth; and
    an antiproliferative coating above and in contact with the prohealing coating that is above the abluminal surface of the stent body, the antiproliferative coating comprising an antiproliferative active agent,
    wherein the prohealing agent is selected from the group consisting of a junction membrane protein vascular endothelial (VE)-cadherin, the active fragment of osteopontin, the antibody CD-133, and any combination thereof.

* * * * *

UNITED STATES PATENT AND TRADEMARK OFFICE
CERTIFICATE OF CORRECTION

| | | |
|---|---|---|
| PATENT NO. | : 8,709,071 B1 | Page 1 of 1 |
| APPLICATION NO. | : 11/864472 | |
| DATED | : April 29, 2014 | |
| INVENTOR(S) | : Huang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 407 days.

Signed and Sealed this
Twenty-first Day of July, 2015

Michelle K. Lee
*Director of the United States Patent and Trademark Office*